(12) United States Patent
Fujikura et al.

(10) Patent No.: US 6,293,908 B1
(45) Date of Patent: Sep. 25, 2001

(54) MOUTHPIECE AND INSERTION ASSISTING DEVICE FOR ENDOSCOPE

(75) Inventors: Tetsuya Fujikura; Haruo Akiba, both of Omiya (JP)

(73) Assignee: Fuji Photo Optical Co., Ltd., Saitama (JP)

(*) Notice: Subject to any disclaimer, the term of this patent is extended or adjusted under 35 U.S.C. 154(b) by 0 days.

(21) Appl. No.: 09/501,258

(22) Filed: Feb. 9, 2000

(30) Foreign Application Priority Data

Feb. 12, 1999  (JP) .................................................. 11-034301
Feb. 22, 1999  (JP) .................................................. 11-043656
Feb. 22, 1999  (JP) .................................................. 11-043657

(51) Int. Cl.$^7$ ...................................................... A61B 1/00
(52) U.S. Cl. ........................... 600/114; 120/861; 606/108
(58) Field of Search ...................... 600/114; 128/200.24, 128/859, 861; 606/108

(56) References Cited

U.S. PATENT DOCUMENTS 5,390,661 * 2/1995 Griffith et al. ....................... 606/108

FOREIGN PATENT DOCUMENTS

A-10-234656   9/1998  (JP) .

* cited by examiner

Primary Examiner—John Mulcahy
(74) Attorney, Agent, or Firm—Oliff & Berridge, PLC

(57) ABSTRACT

According to the present invention, a fixing member is integrated with a mouthpiece body through slide grooves and a rotational groove, and this improves the portability. Moreover, a guide tube can easily be fixed to the mouthpiece body only by rotating the fixing member with the rotational groove. Furthermore, an index is formed on the outer peripheral surface of the guide tube. The index is composed of scale lines formed at regular intervals and scale numbers formed at predetermined scale lines. The scale numbers represent the distances from a front end of the guide tube to the scale line, and the distances from a back end of the guide tube to the scale line. The index of the guide tube is used in combination with an index formed on an endoscope insertion part, and this makes it possible to correctly recognize the insertion length of the endoscope insertion part inserted into a body cavity of a subject.

4 Claims, 15 Drawing Sheets

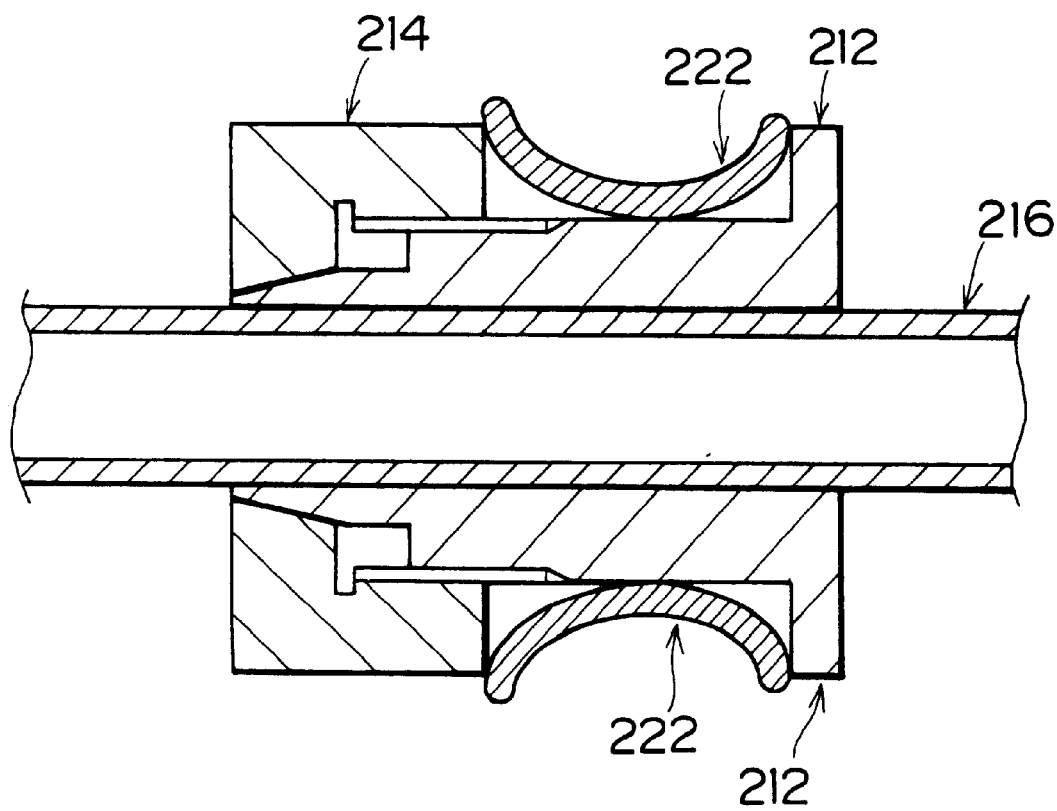
F I G. 1 4

MOUTHPIECE AND INSERTION ASSISTING DEVICE FOR ENDOSCOPE

BACKGROUND OF THE INVENTION

1. Field of the Invention

The present invention relates generally to a mouthpiece and an insertion assisting device for an endoscope. More particularly, the present invention relates to a mouthpiece and an insertion assisting device for an endoscope for assisting oral examination of the small intestines.

2. Description of Related Art

As disclosed in Japanese Patent Provisional Publication No. 10-234656, a guide tube for guiding an insertion part of an endoscope into a body cavity is attached to a mouthpiece for use in the examination of a small intestine.

In the mouthpiece, the guide tube is inserted into an insertion hole formed in a mouthpiece body, and a fixing member is fitted in a cut groove connected to the insertion hole so that the guide tube can be fixed to the mouthpiece body. The Japanese Patent Provisional Publication No. 10-234656 also discloses an example wherein a ring-shaped fixing member is engaged with the mouthpiece body, and is tightened to the mouthpiece body so that the guide tube can be fixed to the mouthpiece body.

The conventional mouthpiece, however, is not easy to carry since the fixing member fitted in the cut groove is separate from the mouthpiece body. The fixing member engaged with the mouthpiece body is easy to carry since it is handled together with the mouthpiece body. However, it takes a long time to fix the guide tube since the fixing member has to be tightened to the mouthpiece body.

The conventional guide tube is inserted from the mouth of a subject to the small intestine. The fixing member fixes the guide tube to the mouthpiece body after the insertion length of the guide tube is adjusted. More specifically, the mouthpiece for use in the examination of the small intestine is composed of the mouthpiece body and the fixing member.

The conventional mouthpiece, however, requires various kinds of mouthpiece bodies with different sizes of parts to be held in the mouths of the subjects for different sizes of mouths. The mouthpiece body has to be machined for the purpose of fixing the guide tube. If various kinds of mouthpiece bodies are prepared, the cost is increased very much. The mouthpiece body is ordinarily bulky, and it is therefore complicated to maintain the mouthpiece if various kinds of mouthpieces are prepared.

An index indicating an insertion length of an endoscope insertion part inserted in the body cavity of the subject is formed on the endoscope insertion part. This makes it possible for an operator to recognize the insertion length of the endoscope insertion part and to specify the position of a pathological area confirmed by the endoscope.

If the conventional guide tube is used, however, the index formed on the endoscope insertion part is concealed by the guide tube, and this makes it impossible to know the insertion length of the endoscope insertion part.

SUMMARY OF THE INVENTION

It is therefore an object of the present invention to provide a mouthpiece for an endoscope, which is excellent in portability and enables a guide tube to be fixed easily.

It is another object of the present invention to provide a mouthpiece for an endoscope, which is easy to manage and reduces a cost.

It is another object of the present invention to provide an insertion assisting device of an endoscope which makes it possible to correctly know the insertion length of an endoscope insertion part.

The above objects can be accomplished by providing a mouthpiece for an endoscope, comprising a mouthpiece body that has an insertion hole into which a guide tube for guiding an endoscope insertion part is inserted, and a fixing member for fixing said guide tube inserted into said insertion hole of said mouthpiece body to said mouthpiece body, said mouthpiece wherein: a large hole and a small hole are formed in said fixing member, said large hole and said small hole being connected to one another; said fixing member slides between such a first position that said insertion hole of said mouthpiece body overlaps said large hole of said fixing member and such a second position that said insertion hole of said mouthpiece body overlaps said small hole of said fixing member, said fixing member being attached to said mouthpiece body in such a manner as to rotate at said second position; and said guide tube is inserted into said insertion hole of said mouthpiece body and said large hole of said fixing member at said first position, and then said fixing member is slid from said first position to said second position and is rotated by a predetermined amount at said second position to thereby hold said guide tube between an inner periphery of said insertion hole and an inner periphery of said small hole to fix said guide tube to said mouthpiece body.

According to the present invention, the fixing member is positioned at such a first position that the large hole of the fixing member overlaps the insertion hole of the mouthpiece body so that the guide tube can be fixed to the mouthpiece body and the fixing member. Therefore, the guide tube is attached to the mouthpiece body and the fixing member. Since the guide tube is not fixed to the mouthpiece body, the guide tube is inserted into the body cavity.

To fix the guide tube to the mouthpiece body, the fixing member is sled first and is positioned at such a second position that the small hole of the fixing member overlaps the insertion hole of the mouthpiece body. At this time, the guide tube is elastically deformed by the inner periphery of the insertion hole and the inner periphery of the small hole, but the guide tube is not fixed to the mouthpiece body since the fixing member moves from the second position to the first position by a restoration force of the guide tube.

The fixing member positioned at the second position is rotated by a predetermined amount to prevent the fixing member from sliding. Consequently, the fixing member never moves toward the first position, and thus, the guide tube is held in the state of being pressed between the inner periphery of the insertion hole and the inner periphery of the small hole. Therefore, the guide tube is surely fixed to the mouthpiece body.

As stated above, the mouthpiece of the present invention is excellent in portability since the fixing member is slidably and rotatably attached to the mouthpiece body. Moreover, the guide tube can easily be fixed to the mouthpiece body only by rotating the fixing member.

The above objects can also be accomplished by providing a mouthpiece for an endoscope, comprising: a mouthpiece body that has an insertion hole into which a guide tube for guiding an endoscope insertion part is inserted; a tooth contact member detachably mounted at an outer periphery of said mouthpiece body, said tooth contact member being held in a mouth of a subject; and a fixing member for fixing said guide tube inserted into said insertion hole of said mouthpiece body to said mouthpiece body.

According to the present invention, the tooth contact member of the mouthpiece is formed independently of the mouthpiece body. Thus, it is only necessary to provide various kinds of tooth contact members correspondingly to various sizes of mouths, and the mouthpiece body can be used commonly for various sizes of mouths. Unlike the mouthpiece body, the tooth contact member does not have to be machined for fixing the guide tube, and therefore, the mouthpiece for the endoscope according to the present invention can be used for various sizes of mouths at a low cost. According to the present invention, it is necessary to only provide various kinds of tooth contact members which are smaller in weight and size than the mouthpiece body. Thus, the mouthpiece can be managed more easily in comparison to the case where various kinds of mouthpieces are prepared.

According to the present invention, the tooth contact member of the mouthpiece is fixed to the mouthpiece body at the same time as the guide tube is fixed to the mouthpiece body by the fixing member. Thus, the tooth contact member can be fixed easily.

The above objects can also be accomplished by providing an insertion assisting device for an endoscope for assisting oral and percutaneous insertion of an endoscope insertion part into a body cavity, said insertion assisting device wherein: an index indicating an insertion length of said insertion assisting device in the body cavity or an index indicating an insertion length of said endoscope insertion part is formed on a surface of said insertion assisting device.

According to the present invention, the index indicating the insertion length of the endoscope insertion part is formed on the insertion assisting device, so that the operator can correctly know the insertion length of the endoscope insertion part even if the insertion assisting device is attached to the endoscope insertion part. Moreover, the index indicating the insertion length of the insertion assisting device in the body cavity is formed on the insertion assisting device, so that the operator can correctly know the insertion length of the insertion assisting device.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 14 is an explanation drawing showing a tooth contact member shaped differently from the tooth contact member in FIG. 11;

DETAILED DESCRIPTION OF THE PREFERRED EMBODIMENT

This invention will be described in further detail by way of example with reference to the accompanying drawings.

Figure 1:
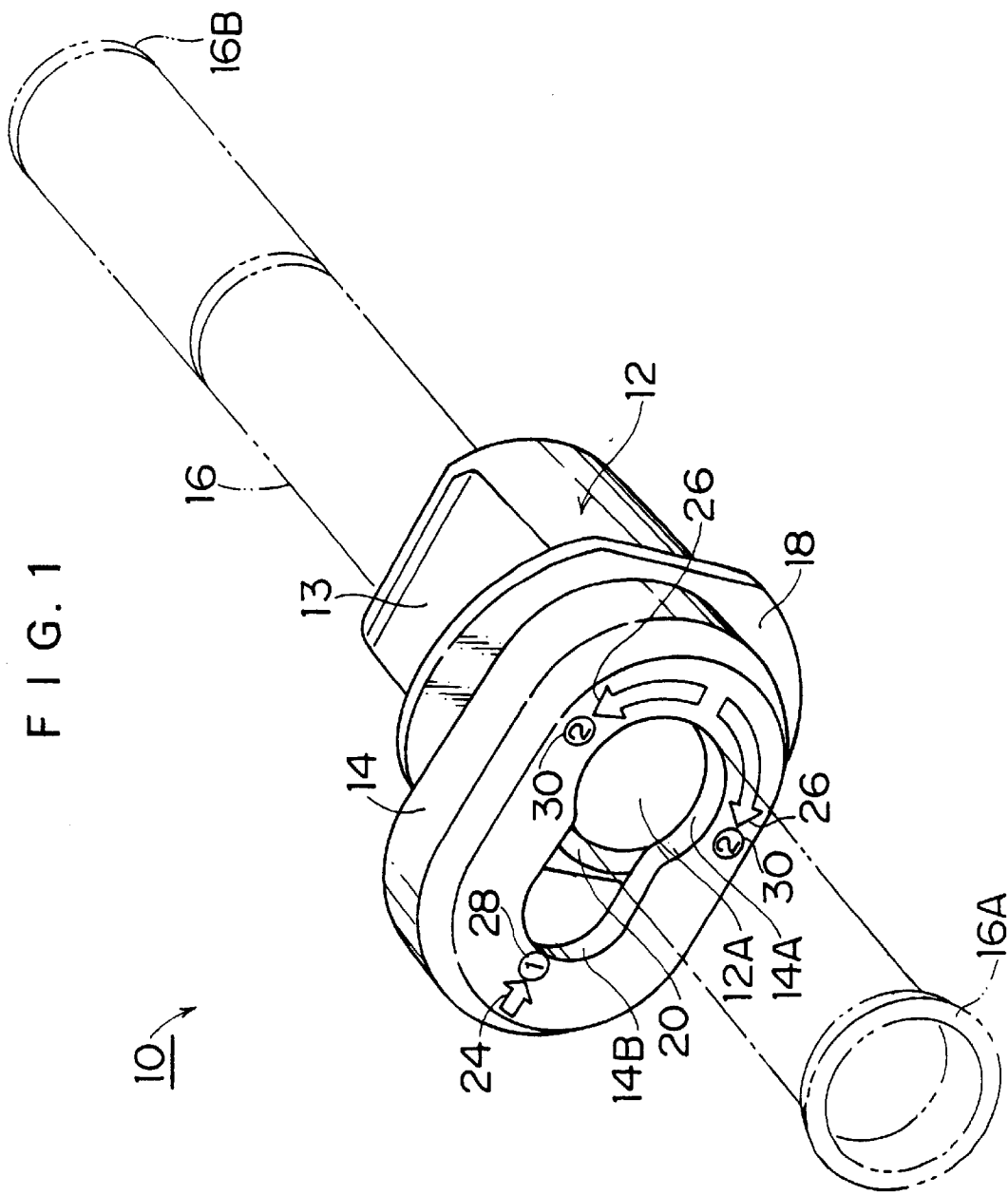
FIG. 1 is a perspective view showing a mouthpiece for an endoscope according to an embodiment of the present invention.
Figure 2:
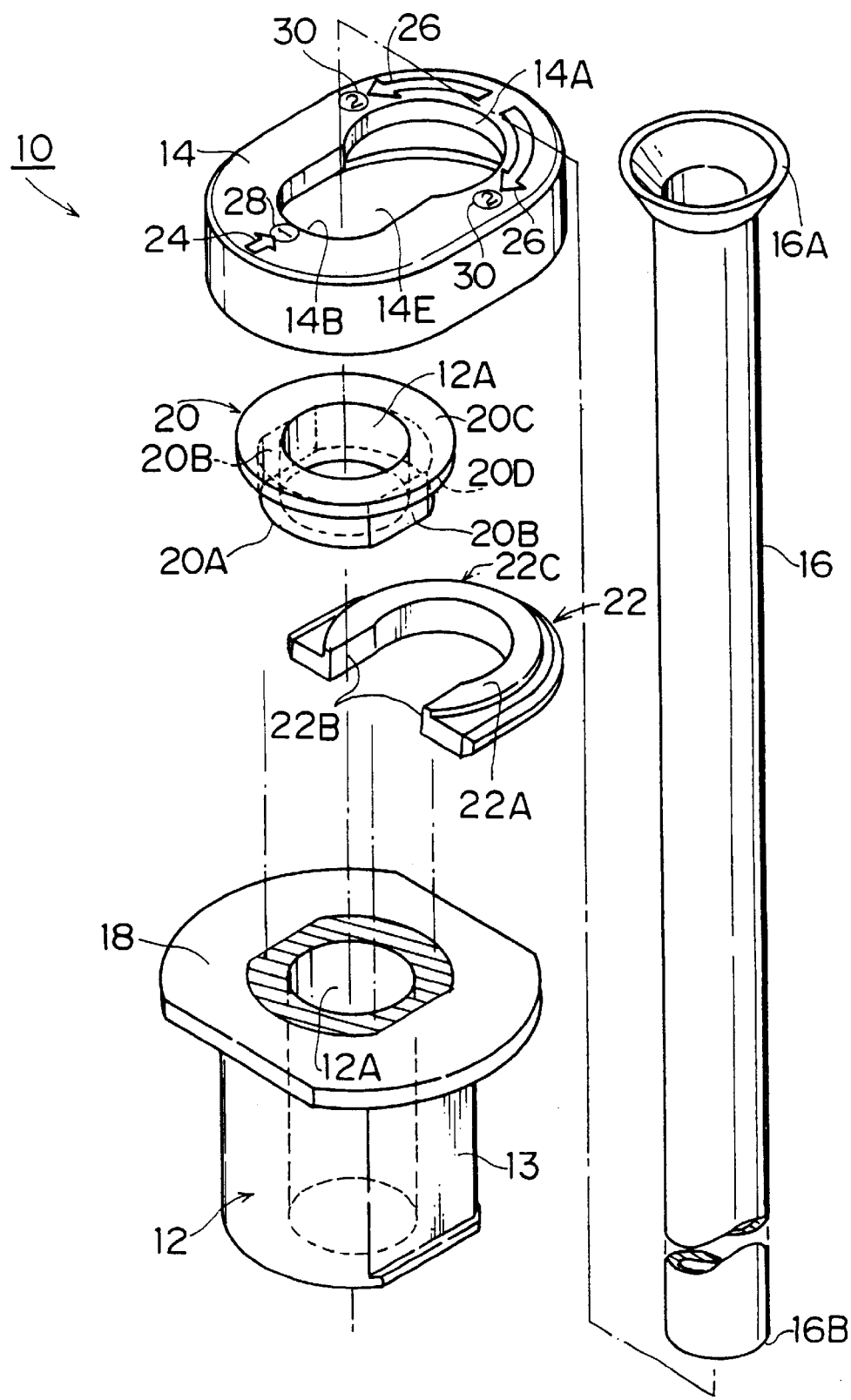
FIG. 2 is a perspective view showing the assembly of the mouthpiece for the endoscope in FIG. 1.
Figure 3:
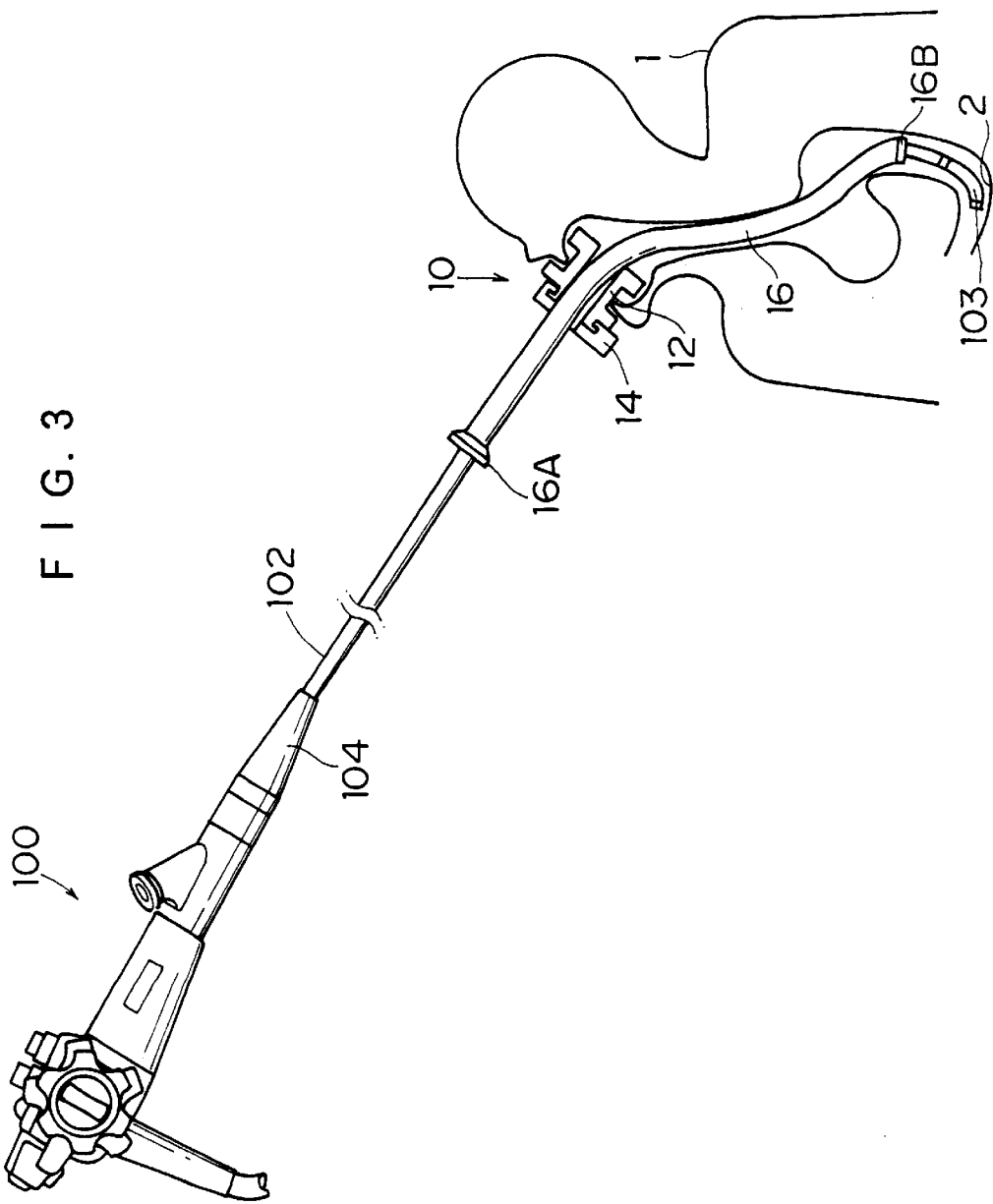
FIG. 3 is a perspective view showing how to handle the mouthpiece for the endoscope in FIG. 1.

FIG. 1 is a perspective view showing the entire endoscope mouthpiece 10 for use in an endoscopic examination of small intestines according to a preferred embodiment of the present invention. FIG. 2 is a perspective view showing the assembly of the mouthpiece 10 in FIG. 1. FIG. 3 is a view showing the state wherein the mouthpiece 10 is used.

As shown in FIGS. 1 and 2, the mouthpiece 10 is composed of a mouthpiece body 12 and a fixing member 14. A guide tube 16 is inserted into the mouthpiece body 12 and the fixing member 14. The mouthpiece body 12 has an insertion hole 12A, into which the guide tube 16 is inserted. The fixing member 14 has an insertion hole (corresponding to a large hole) 14A, into which the guide tube 16 is inserted, and a fixing hole (corresponding to a small hole) 14B connected to the insertion hole 14A. The insertion holes 12A, 14A and the fixing hole 14B will be described later.

Referring next to FIG. 3, there will now be explained a method of handling the mouthpiece 10. Before a small intestine endoscope 100 is inserted into a subject 1, an endoscope insertion part 102 is inserted into the guide tube 16. Then, the guide tube 16 is drawn along the endoscope insertion part 102 toward a hand control part 104. The front end of the hand control part 104 is fitted into a scope insertion opening 16A of the guide tube 16.

Next, the endoscope insertion part 102 is inserted into a predetermined position in a body cavity while the subject 1 is holding the mouthpiece body 12 in his or her mouth. Then, the guide tube 16 is inserted along the endoscope insertion part 102 into the body cavity. The insertion of the guide tube 16 is stopped when an end 16B of the guide tube 16 is positioned in a descending part of duodenum 2. Then, the fixing member 14 of the mouthpiece 10 fixes the guide tube 16 to the mouthpiece body 12. The endoscope insertion part 102 is inserted more to enable the endscopic examination in the depths of the small intestine by the endoscope 100. The mouthpiece 10 is handled in the abovedescribed manner.

A flange 18 is formed at the outer circumference of the mouthpiece body 12. A holding part 13 is formed at one side of the flange 18, and a projecting pipe 20 is formed at the other side of the flange 18. The insertion hole 12A is formed through the mouthpiece 12 from the holding part 13 to the projecting pipe 20. The guide tube 16 is inserted into the insertion hole 12A whose diameter is larger than the outer diameter of the guide tube 16.

Figure 4:
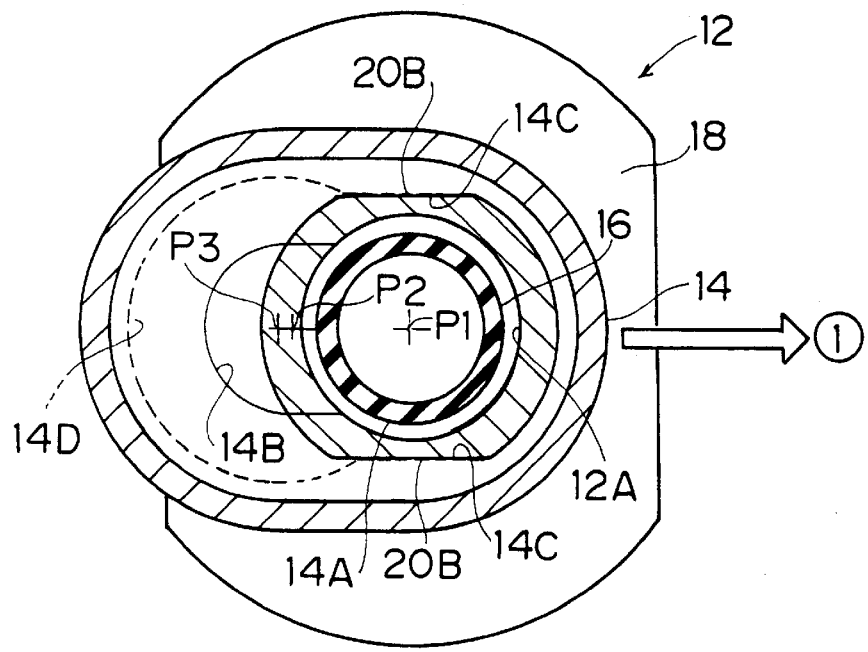
FIG. 4 is an explanation drawing showing how to operate the mouthpiece for the endoscope in FIG. 1.

An arc groove 20A is formed at the outer circumference of the projecting pipe 20, and a pair of flat surfaces 20B is formed oppositely to one another in the groove 20A. As shown in FIG. 4, the flat surfaces 20B are fitted with a pair of slide grooves 14C formed in the inner peripheral surface of the fixing member 14. Therefore, the fixing member 14 is able to slide in a direction indicated by an arrow ① in FIG. 4 with respect to the mouthpiece body 12. In FIG. 4, the fixing member 14 is located at such a position (a first position) that the insertion hole 14A of the fixing member 14 can overlap the insertion hole 12A of the mouthpiece body 12. The diameter of the insertion hole 14A of the fixing member 14 is larger than the outer diameter of the guide tube 16 as is the case with the insertion hole 12A. The guide tube 16 inserted into the insertion holes 12A, 14A is capable of moving freely with respect to the mouthpiece body 12. Reference numeral P1 in FIG. 4 denotes a central axis of the insertion hole 14A; P2, a central axis of a fixing hole 14B; P3, a central axis of a rotational groove 14D.

Figure 6:
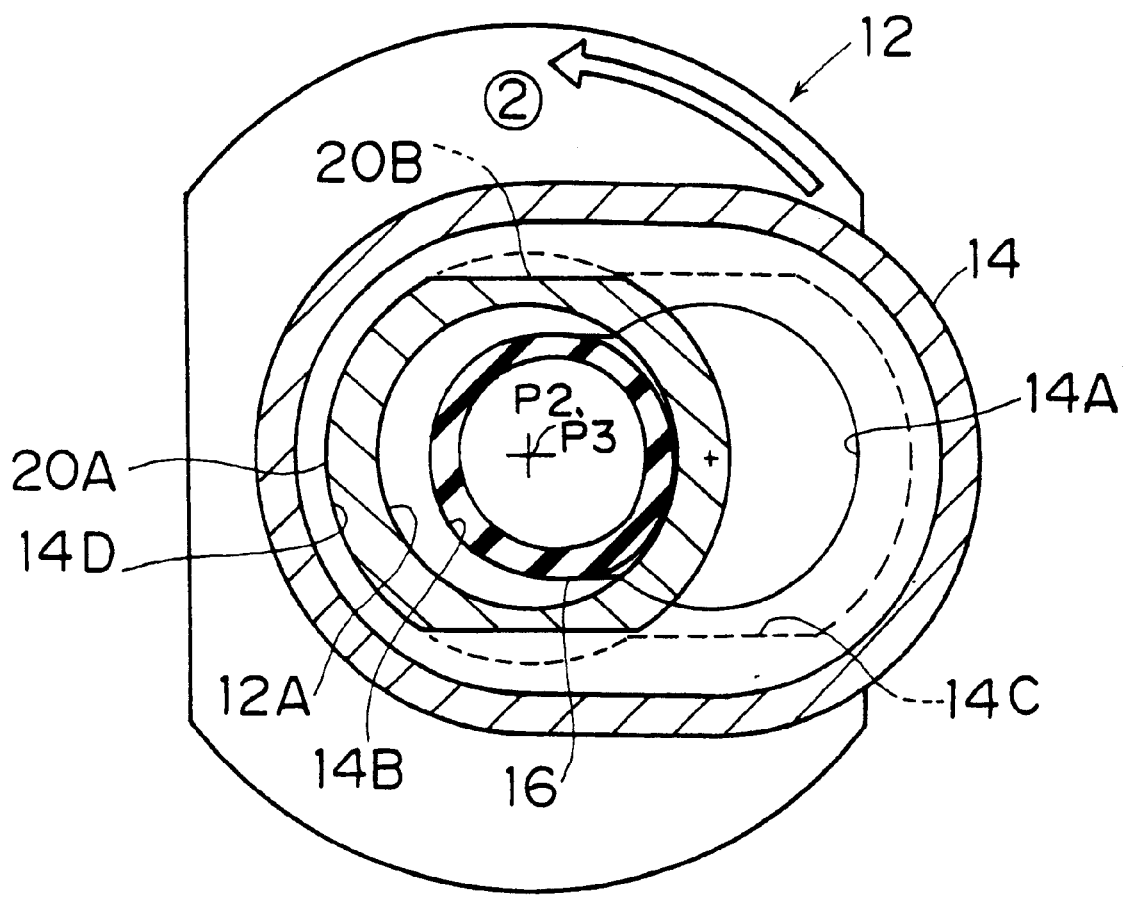
FIG. 6 is an explanation drawing showing how to operate the mouthpiece for the endoscope in FIG. 1.

On the other hand, the rotational groove 14D is formed at the inner circumference of the fixing member 14, and is engaged with the groove 20A of the projecting pipe 20. When the fixing member 14 is positioned as shown in FIG. 6, the fixing member 14 can rotate with respect to the mouthpiece body 12. In FIG. 6, the fixing member 14 is positioned at such a position (a second position) that a fixing hole 14B of the fixing member 14 can overlap the insertion hole 12A of the mouthpiece body 12. The diameter of the fixing hole 14B of the fixing member 14 is smaller than the outer diameter of the guide tube 16, and thus, the guide tube 16 is pressed between the inner peripheral surface of the insertion hole 12A and the inner peripheral surface of the fixing hole 14B. When the fixing member 14 is rotated by 90° in a direction indicated by an arrow ② in FIG. 6, the guide tube 16 is held in the state of being pressed between the inner peripheral surface of the insertion hole 12A and the inner peripheral surface of the fixing hole 14B. More specifically, the guide tube 16 is fixed to the mouthpiece 10 by the fixing member 14. When the fixing member 14 is rotated by 90° in the same direction or in the opposite direction, the guide tube 16 is released so that the guide tube 16 can become free with respect to the mouthpiece body 12.

On the other hand, the mouthpiece 10 has a U-shaped slip prevention member 22 as shown in FIG. 2. The slip prevention member 22 is fixed to a bottom opening 14E of the fixing member 14 while the flat surfaces 20B of the projecting pipe 20 are fitted with side parts 22B, 22B of the slip prevention member 22. The slip prevention member 22 connects the fixing member 14 and the projecting pipe 20. When an external force is applied to the fixing member 14 to slip the fixing member 14, an upper surface 22A of a convex part 22C comes in contact with a lower surface 20D of a flange 20C of the projecting pipe 20. This prevents the fixing member 14 from slipping.

As shown in FIGS. 1 and 2, arrows 24, 26, 26 indicating the operating directions of the fixing member 14 and marks ①, ②, ② denoted by reference numerals 28, 30, 30 indicating the operating order of the fixing member 14 are impressed on the top surface of the fixing member 14.

A description will now be given of the operation of the mouthpiece 10 that is constructed in the above-mentioned manner.

To attach the guide tube 16 to the mouthpiece body 12 and the fixing member 14, the fixing member 14 is positioned at the first position so that the insertion hole 14A of the fixing member 14 can overlap the insertion hole 12A of the mouthpiece body 12 as shown in FIGS. 1 and 4. Then, the guide tube 16 is inserted into the insertion holes 12A, 14A. Consequently, the guide tube 16 is attached to the mouthpiece body 12 and the fixing member 14. At this time, the guide tube 16 is not fixed to the mouthpiece body 12, and thus, the guide tube 16 is inserted into the body cavity as shown in FIG. 3.

Figure 5:
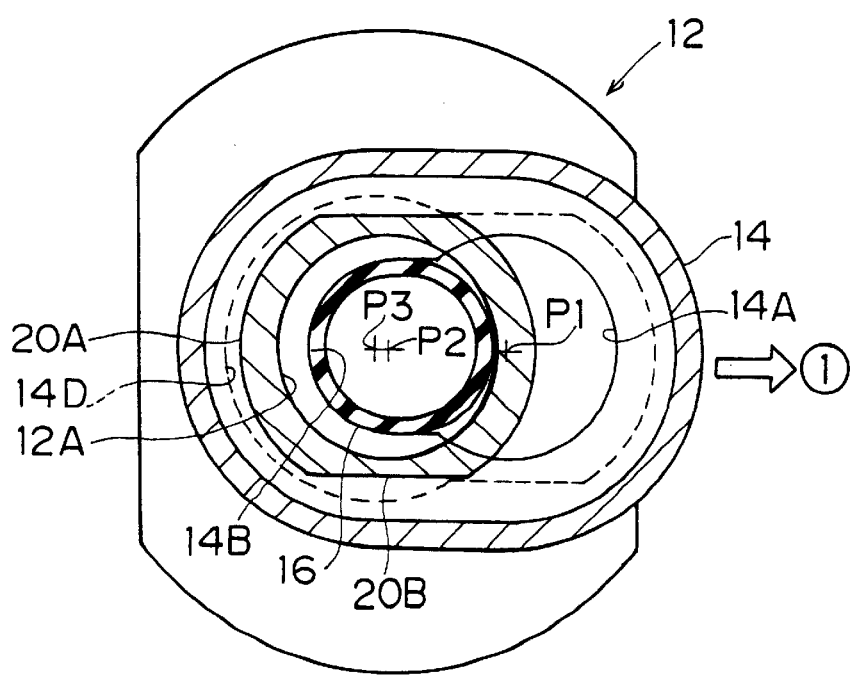
FIG. 5 is an explanation drawing showing how to operate the mouthpiece for the endoscope in FIG. 1.

To fix the guide tube 16 to the mouthpiece body 12, the fixing member 14 is slid in a direction indicated by an arrow ① in FIG. 4 with the slide grooves 14C, and the fixing member 14 is positioned at the second position as shown in FIG. 5 so that the fixing hole 14B of the fixing member 14 can overlap the insertion hole 12A of the mouthpiece body 12. Then, the fixing member 14 is further slid in the same direction, so that the inner peripheral part of the insertion hole 12A and the inner peripheral part of the fixing hole 14B elastically deform and press the guide tube 16 therebetween.

If the guide tube 16 were made of hard material, the guide tube 16 would be fixed to the mouthpiece body 12 in FIG. 6. The guide tube 16, however, is made of soft material such as rubber, and thus, the fixing member 14 is moved from the position in FIG. 6 to the position in FIG. 5 due to a restoration force of the guide tube 16. For this reason, the guide tube 16 is not fixed to the mouthpiece body 12.

Figure 7:
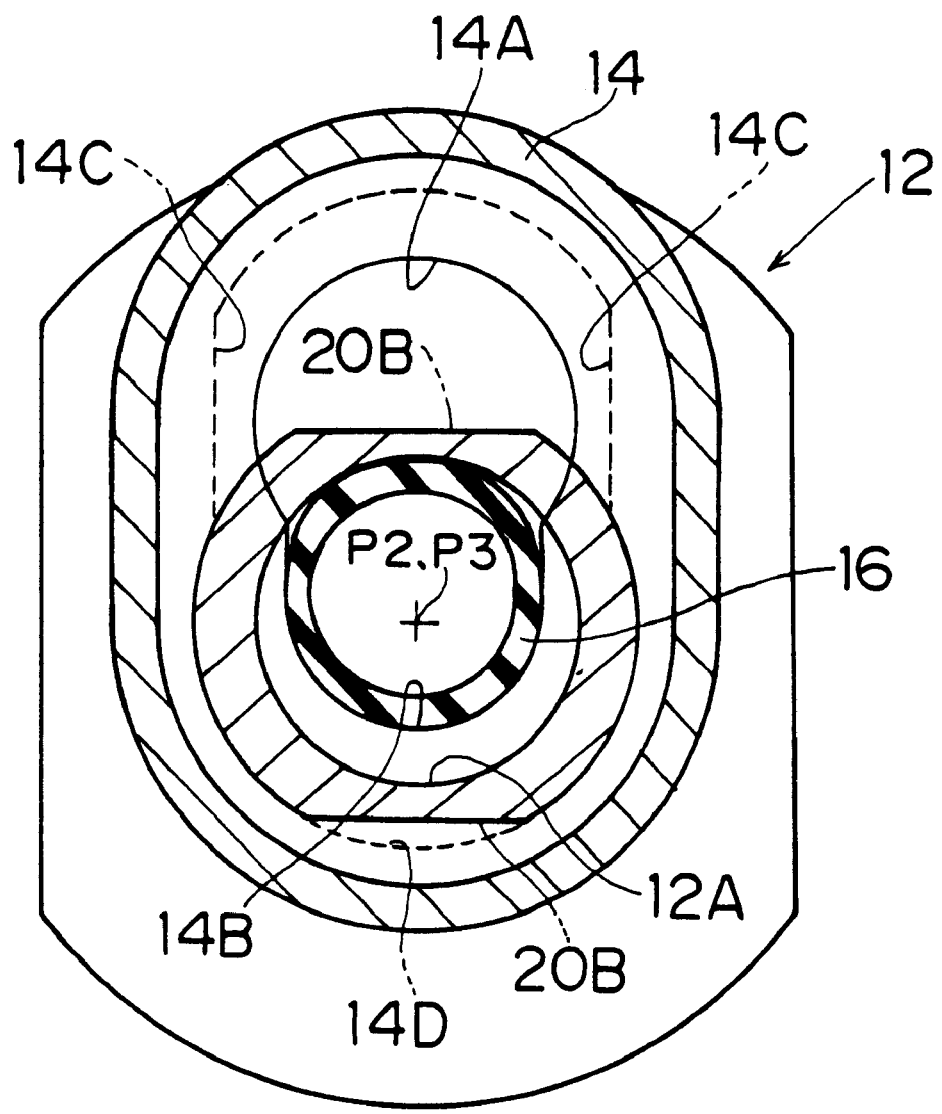
FIG. 7 is an explanation drawing showing how to operate the mouthpiece for the endoscope in FIG. 1.

To address this problem, the fixing member 14 positioned as shown in FIG. 6 is rotated by e.g., 90° in a direction indicated by the arrow ② to position the fixing member 14 as shown in FIG. 7. Consequently, the slide grooves 14C of the fixing member 14 are moved back from the flat surfaces 20B of the projecting pipe 20, and thus, the fixing member 14 is never positioned as shown in FIG. 5. The guide tube 16 is held while being pressed between the inner peripheral part of the insertion hole 12A and the inner peripheral part of the fixing hole 14B. Thus, the guide tube 16 is fixed to the mouthpiece body 12 without fail.

As set forth hereinabove, the mouthpiece 10 of this embodiment is constructed in such a manner that the mouthpiece body 12 and the fixing member 14 are connected and integrated through the slide grooves 14C and the rotational groove 14D, and this improves the portability of the mouthpiece 10. Moreover, the guide tube 16 can easily be fixed to the mouthpiece body 12 only by rotating the fixing member 14 with the rotational groove 14D.

In this embodiment, the fixing member 14 is rotated counterclockwise in FIG. 6 to fix the guide tube 16, but the fixing member 14 may also be rotated clockwise to fix the guide tube 16.

In this embodiment, the arrows 24, 26, 26 indicating the operating directions of the fixing member 14 and the marks ①, ②, ② denoted by reference numerals 28, 30, 30 indicating the operating order of the fixing member 14 are impressed on the top surface of the fixing member 14 to form an index part. The index part may also be formed by impressing dots 40, 42, 44 as shown in FIG. 8.

Figures 8A, 8B:
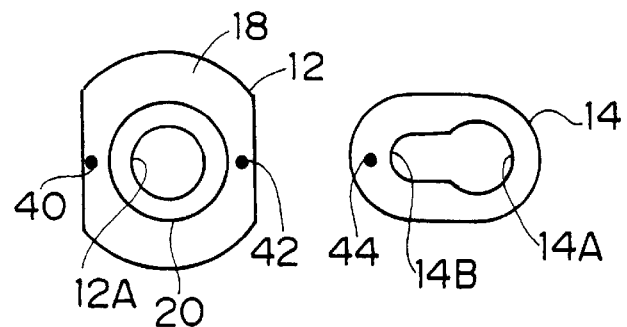
FIGS. 8(A) and 8(B) are explanation drawing s showing indexes for med on a mouthpiece body and a fixing member.

In FIG. 8(A), the dots 40, 42 are impressed symmetrically with respect to the insertion hole 12A on the flange 18 of the mouthpiece body 12. In FIG. 8(B), the dot 44 is impressed at the left side of the fixing hole 14B of the fixing member 14.

Figures 9A, 9B, 9C:
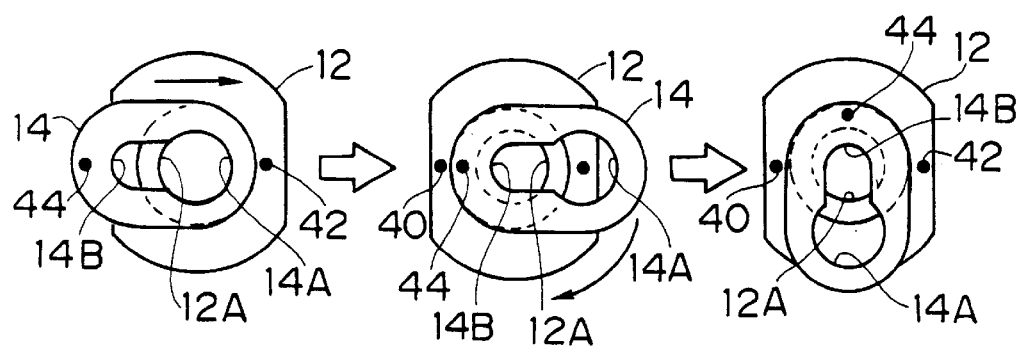
FIGS. 9(A), 9(B), 9(C), 9(D) and 9(E) are transition views describing how to operate the mouthpiece for the endoscope in FIG. 8.

In the mouthpiece 10 with the dots 40, 42, 44, the dots 42, 44 are exposed as shown in FIG. 9(A) when the fixing member 14 is at the first positioned where the insertion hole 12A and the insertion hole 14A overlap. More specifically, the guide tube 16 can be inserted into the mouthpiece 10 in the state where the dots 42, 44 are exposed.

Then, the fixing member 14 is slid to the right to the second position so that the insertion hole 12A can overlap the fixing hole 14B. When the fixing member 14 is further pressed in the same direction in order to elastically deform the guide tube 16, the dot 40 is exposed as shown in FIG. 9(B). The exposure of the dot 40 makes it possible to confirm the sliding amount of the fixing member 14, and shows that the fixing member 14 is rotatable (i.e., the guide tube 16 can be fixed).

When the fixing member 14 is rotated clockwise by 90°, all the dots 40, 42, 44 are exposed as shown in FIG. 9(C). The exposure of the dots 40, 42, 44 makes it possible to confirm the rotating amount of the fixing member 14, and shows that the guide tube 16 is fixed to the mouthpiece body 12.

Figures 9D, 9E:
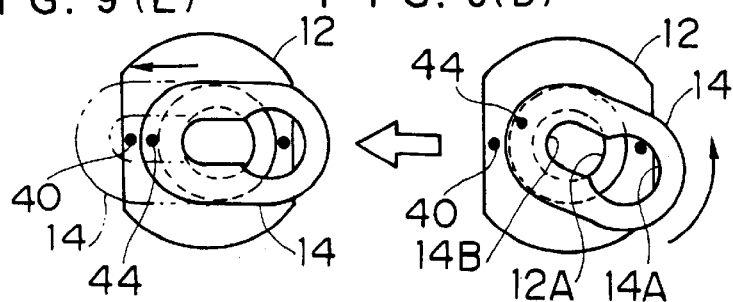

To release the guide tube 16, the fixing member 14 is rotated counterclockwise by 90° as shown in FIG. 9(D) and is slid to the left as shown in FIG. 9(E). This positions the fixing member 14 at the first position, and the guide tube becomes free.

In the mouthpiece 10 of this embodiment, the mouthpiece body 12, the fixing member 14 and the slip prevention member 22 are made of heat-resistant material (e.g., imidopolyether) and the slip prevention member 22 is adhered to the fixing member 14 by a heat-resistant epoxy adhesive agent so that the mouthpiece 10 can be cleaned in an autoclave (e.g., in heated and pressurized vapor of 2 atmospheres and about 130° C.).

In this embodiment, the diameter of the fixing hole 14B is smaller than the outer diameter of the guide tube 16, but it may be larger than the outer diameter of the guide tube 16. In this case, the sliding amount of the fixing member 14 is set so that an opening area (the size of the hole) enclosed by the insertion hole 12A and the fixing hole 14B when the fixing member 14 is at the second position is smaller than the sectional area of the guide tube 16.

As set forth hereinabove, in the mouthpiece for the endoscope according to the present invention, the fixing member is slidably and rotatably integrated with the mouthpiece body, and this improves the portability of the mouthpiece. The guide tube can easily be fixed to the mouthpiece body only by rotating the fixing member.

Figure 10:
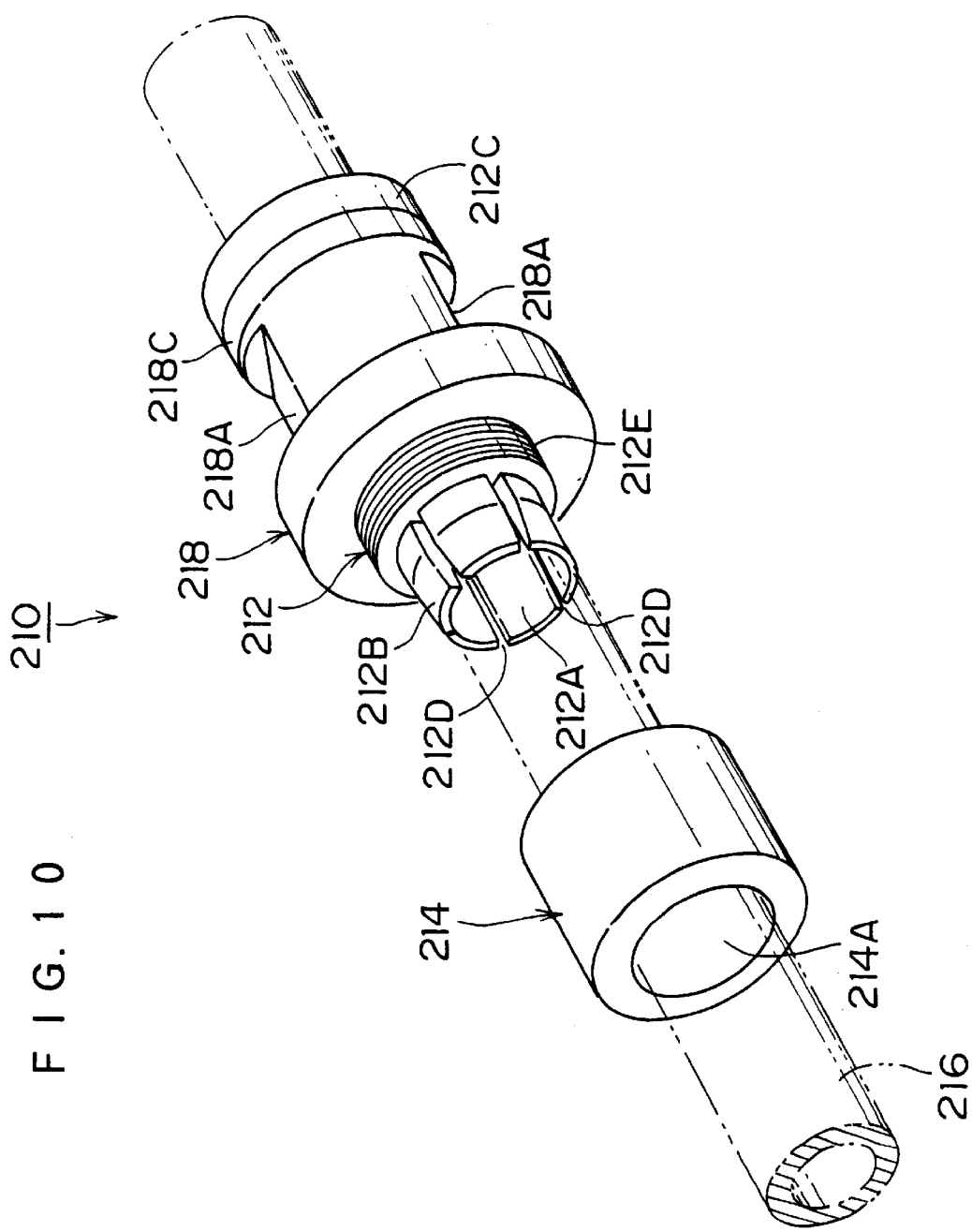
FIG. 10 is a perspective view showing an entire e mouthpiece for an endoscope according to another embodiment of the present invention.
Figure 11:
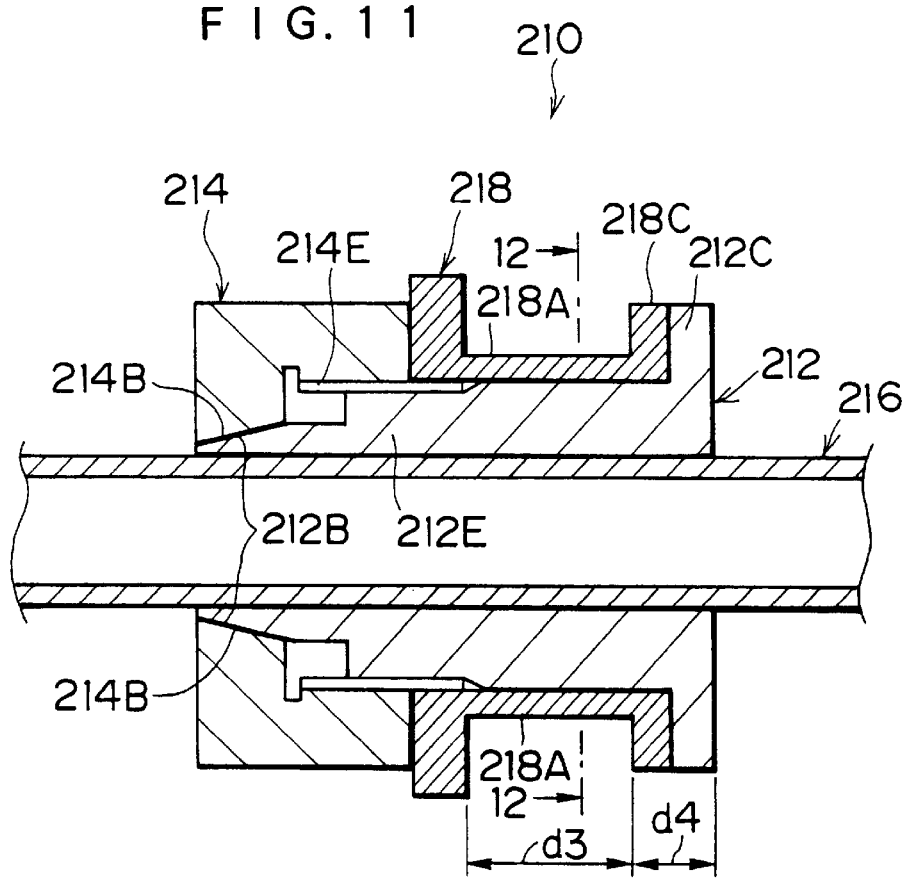
FIG. 11 is a sectional view showing an assembly of the mouthpiece in FIG. 10.

FIG. 10 is a perspective view showing an entire mouthpiece 210 for the endoscope according to this embodiment for use in the endoscopic examination of the small intestine. FIG. 11 is a sectional view of the mouthpiece 210 in FIG. 10, and FIG. 12 is a sectional view taken along a line 12—12.

Figure 12:
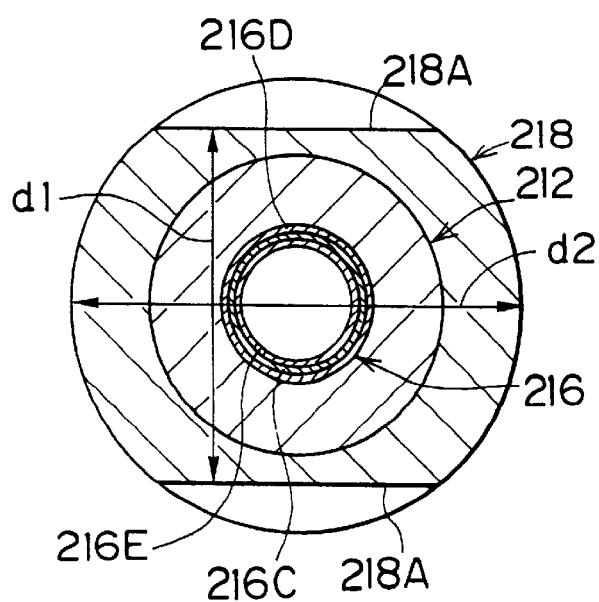
FIG. 12 is a sectional view taken along line 12—12 in FIG. 11.

As shown in FIGS. 10–12, the mouthpiece 212 comprises a mouthpiece body 212, a fixing member 214 and a tooth contact member 218. A guide tube 216 is inserted into the mouthpiece body 212 inserted into the tooth contact member 218, and the fixing member 214. The mouthpiece body 212 has an insertion hole 212A, into which the guide tube 216 is inserted. The fixing member 214 has an insertion hole 214A, into which the guide tube 216 is inserted. A male screw 212E is formed on an outer peripheral surface of the mouthpiece body 212, and a female screw 214E is formed on an inner peripheral surface of the fixing member 214. The male screw 212E is engaged with the female screw 214E.

A flange 212C is formed at one end of the mouthpiece body 212, and a flange 218C of a tooth contact member 218 is in contact with the flange 212C. A conical inclined plane 212B is formed at the other end of the mouthpiece body 212.

A plurality of chips 212D is formed in the inclined plane 212B so that the inclined plane 212B can be deformed inward.

On the other hand, an inclined plane 214B is formed on the inner peripheral surface of the fixing member 214. The inclined plane 214B is steeper than the inclined plane 212B of the mouthpiece body 212. When the fixing member 214 is fitted to the mouthpiece body 212, the inclined plane 214B of the fixing member 214 presses the inclined plane 212B of the mouthpiece body 212, which is deformed inward to fix the guide tube 16.

A pair of flat surfaces 218A is formed oppositely on the peripheral surface of the tooth contact member 218. The subject of examination holds the flat surfaces 218A with his or her mouth. The tooth contact member 218 may take a variety of forms; for example, various kinds of tooth contact member 218 with different flat surface intervals d1 and different outer diameters d2 in FIG. 12 are prepared.

The mouthpiece 210 constructed in the above-mentioned manner is made of material that can be disinfected and sterilized. For example, the mouthpiece body 212, the tooth contact member 218 and the fixing member 214 are made of heat-resistant resin such as imidopolyether resin so that the mouthpiece 210 can be disinfected in an autoclave (in heated and pressurized vapor with 2 atmospheres and 132° C.).

On the other hand, the guide tube 216 is composed of three layers wherein a tube 216C made of resin such as urethane is coated with a chemical-resistant coating 216D and the inner surface of the tube 216C is protected with a lubrication coating 216E as shown in FIG. 12. Normally, the guide tube is about 850 mm long if an elastic part of the endoscope is about 2300 mm long. A disinfectant liquid and body fluids such as gastric juices never encroach on the guide tube 216, which is covered with the chemical-resistant coating 216D, and an endoscope insertion part can be inserted smoothly into the guide tube 216 since the inner surface of the tube 216C is protected with a lubrication coating 216E.

Figure 13:
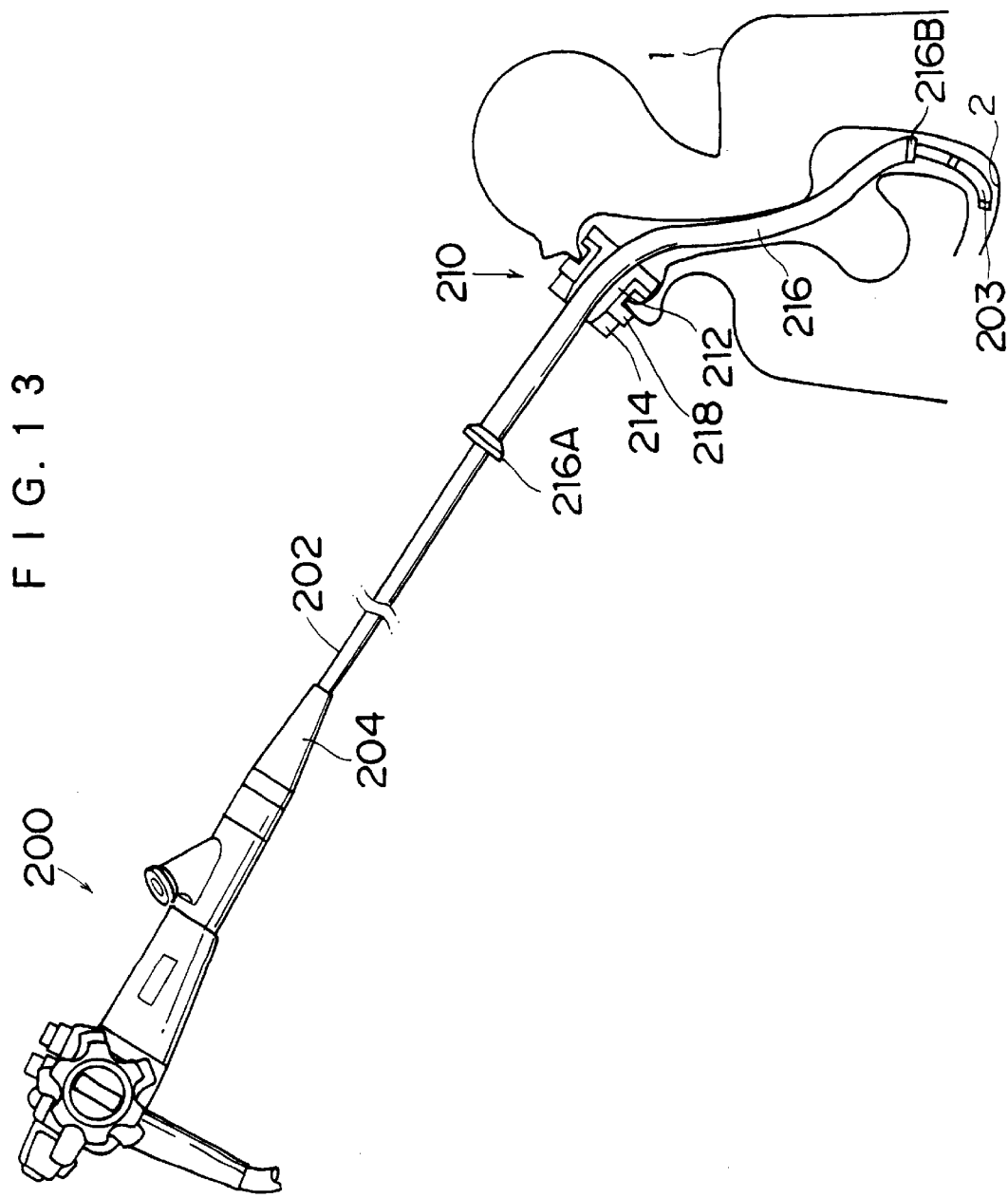
FIG. 13 is an explanation drawing showing how to operate the mouthpiece for the endoscope in FIG. 10.

Referring next to FIGS. 11 and 13, there will now be explained a method of handling the mouthpiece 210. First, the tooth contact member 218 of the mouthpiece 210 is mounted to the mouthpiece body 212, and the fixing member 214 is fitted to the mouthpiece body 212 so that the inner diameter of the inclined plane 212B of the mouthpiece body 212 can be larger than the outer diameter of the guide tube 216.

Next, the guide tube 216 is inserted into the endoscope insertion part 202 before a small intestine endoscope 200 is inserted into the subject 1 as shown in FIG. 13. Then, the guide tube 216 is drawn along the endoscope insertion part 202 toward a hand operation part 204, and the front end of the hand operation part 204 is fitted into a scope insertion opening 216A.

Then, the tooth contact member 218 of the mouthpiece 210 is held in the mouth of the subject 1, and the endoscope insertion part 202 is inserted into a predetermined position in the body cavity. The guide tube 216 is inserted along the endoscope insertion part 202 into the body cavity, and the insertion of the guide tube 216 is stopped when an end 216B of the guide tube 216 is positioned in the descending part of duodenum 2.

Then, the fixing member 214 of the mouthpiece 210 in FIG. 11 is rotated and is fitted to the mouthpiece body 212 and the guide tube 216 is fixed to the mouthpiece body 212. The insertion of the endoscope insertion part 202 in FIG. 13 enables the endoscopic examination in the depths of the small intestine. The mouthpiece 210 is handled in the above-mentioned manner.

A description will now be given of the operation of the mouthpiece 210 constructed in the above-mentioned manner.

As stated above, the mouthpiece 210 is constructed in such a manner that the tooth contact member 218 is formed independently of the mouthpiece body 212. If the mouthpiece body 212 is used for the subjects 1 whose mouths are various sizes, various kinds of tooth contact members 218 directly held in the mouths of the subjects 1 are only prepared. In this case, the mouthpiece body 212 is commonly used for various sizes of mouths. If two kinds of mouthpieces 210 for adults and children are prepared, two kinds of tooth contact members 218 with different flat surface intervals d1 and outer diameters d2 are prepared but only one kind of mouthpiece body 212 and one kind of fixing member 214 are prepared. There is no necessity of machining the tooth contact member 218 while parts of the mouthpiece body 212 for fixing the guide tube 216 (i.e., the inclined plane 212B and the chips 212D) need to be machined, and this reduces the cost compared with the case where various combinations of the mouthpiece bodies 212 and the tooth contact members 218 are prepared. More specifically, the mouthpiece 210 of this embodiment can be used for the subjects 1 whose mouths are various sizes at a low cost. According to the mouthpiece 210 of this embodiment, only the tooth contact member 218 which is easily damaged by the mouth of the subject 1, can be exchanged to another one, and this is very economical. If the tooth contact member 218 can be made of inexpensive material, the tooth contact member 218 can be a disposable.

In the mouthpiece 210 of this embodiment, the fixing member 214 fixes the guide tube 216 and the tooth contact member 218 to the mouthpiece body 212 at a time. Therefore, the fixing operation is never complicated although the tooth contact member 218 is formed independently of the mouthpiece body 212.

In this embodiment, the tooth contact members 218 with different flat surface intervals d1 and outer diameters d2 are prepared, but this invention should not be restricted to this. The tooth contact members 218 may take any other forms. For example, various tooth contact members 218 with different flange lengths d3 and flat surface lengths d4 in FIG. 11 may be prepared. It is also possible to prepare a tooth contact member 222, which is depressed inward as shown in FIG. 14. In this case, it is preferable to prepare the tooth contact members 222 shaped correspondingly to the occlusion of each subject 1. Several kinds of tooth contact members 218 made of different materials may be prepared. For example, the tooth contact member 218 is made of fluororubber, fluoride TPE, or the like. Therefore, the intensity of the tooth contact member 218 and the like may be changed according to a preference of the subject 1. If the tooth contact member 218 is elastic, it can be deformed according to the size of the mouth, and this decreases the kinds of the tooth contact members 218 to be prepared.

Figure 15:
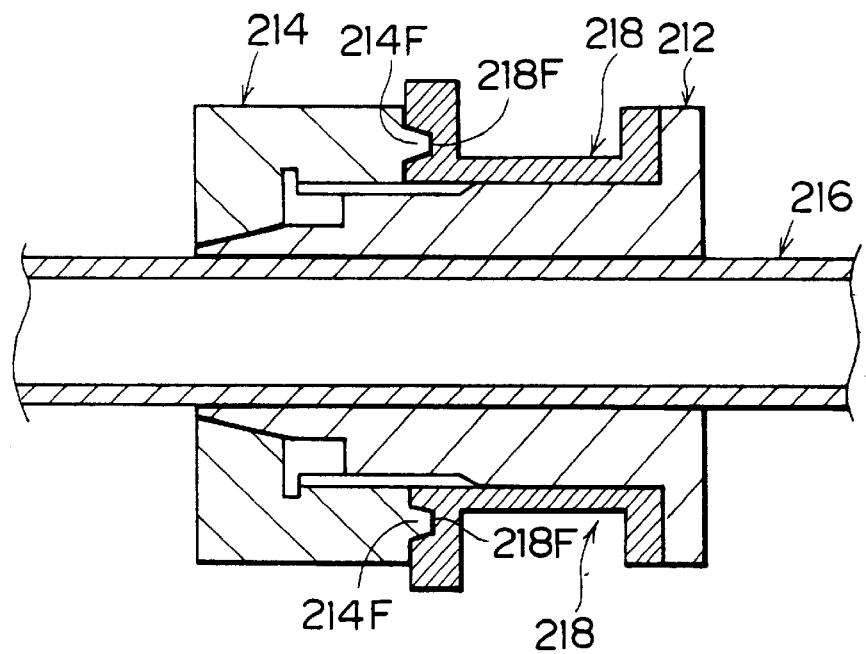
FIG. 15 is an explanation drawing showing a method of positioning the tooth contact member.

In this embodiment, the fixing member 214 may position the tooth contact member 218. For example, as shown in FIG. 15, a connecting part composed of a convex part 214F and a concave part 218F is formed on a surface where the fixing member 214 contacts the tooth contact member 218 in such a manner that an axis of the tooth contact member 218 can surely correspond to axes of the mouthpiece body 212 and the fixing member 214. This prevents the tooth contact member 218 from becoming loose. It is possible to form a connecting part on a surface where the mouthpiece body 212 contacts with the tooth contact member 218. This prevents the rotation of the tooth contact member 218 with respect to the mouthpiece 212.

Figure 16:
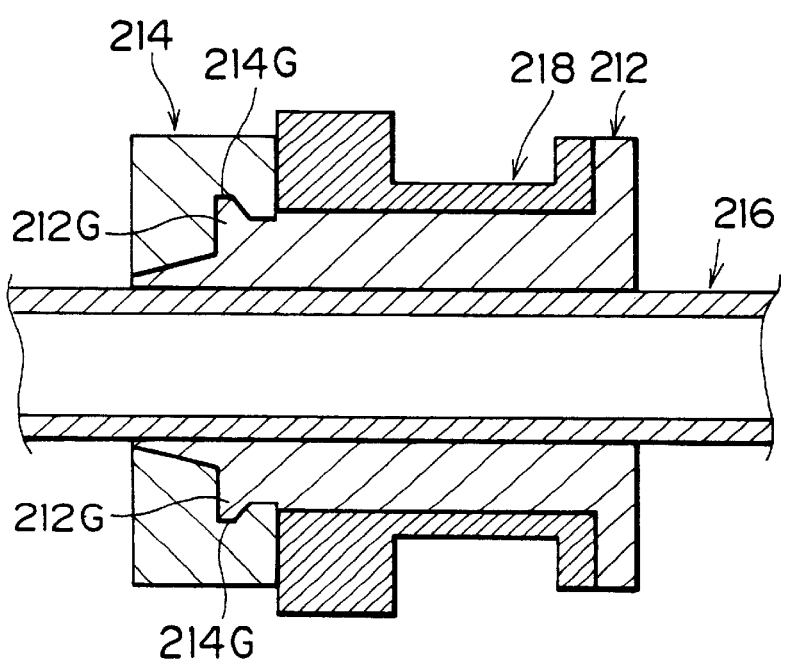
FIG. 16 is an explanation drawing showing a mouthpiece shaped differently from the mouthpiece in FIG. 11.

The fixing member 214 does not necessarily fix the tooth contact member 218 to the mouthpiece body 212 in the method of this embodiment. For example, the fixing member 214 may also fix the tooth contact member 218 to the mouthpiece body 212 as shown in FIG. 16. In the case of a mouthpiece in FIG. 16, a convex part 212G and a concave part 214G are formed instead of the male screw 212E and the female screw 214E. The mouthpiece body 212 is fixed to the fixing member 214 by engaging the convex part 212G with the concave part 214G.

In this embodiment, the fixing member 214 fixes the guide tube 216 and the tooth contact member 218 to the mouthpiece body 212 at a time, but the guide tube 216 and the tooth contact member 218 may also be fixed to the mouthpiece body 212 independently of one another. For example, the tooth contact member 218 is formed by cutting a part of an annular member (substantially shaped like C). The cut part of the tooth contact member 218 is fitted in the mouthpiece body 212 first, so that the tooth contact member 218 can be fixed to the mouthpiece body 212.

As set forth hereinabove, the endoscope mouthpiece of the present invention has the tooth contact member, which is formed independently of the mouthpiece body. Therefore, various kinds of tooth contact members only must be prepared for various sizes of mouths. The mouthpiece body can be commonly used for various sizes of mouths. This reduces the cost of the mouthpiece compared with the case where various combinations of the mouthpiece body and the tooth contact member integrated with one another are prepared. Moreover, the mouthpieces can be managed easily. According to the present invention, the fixing member for fixing the guide tube to the mouthpiece body can easily fix the tooth contact member to the mouthpiece body in a simple operation.

Figure 17:
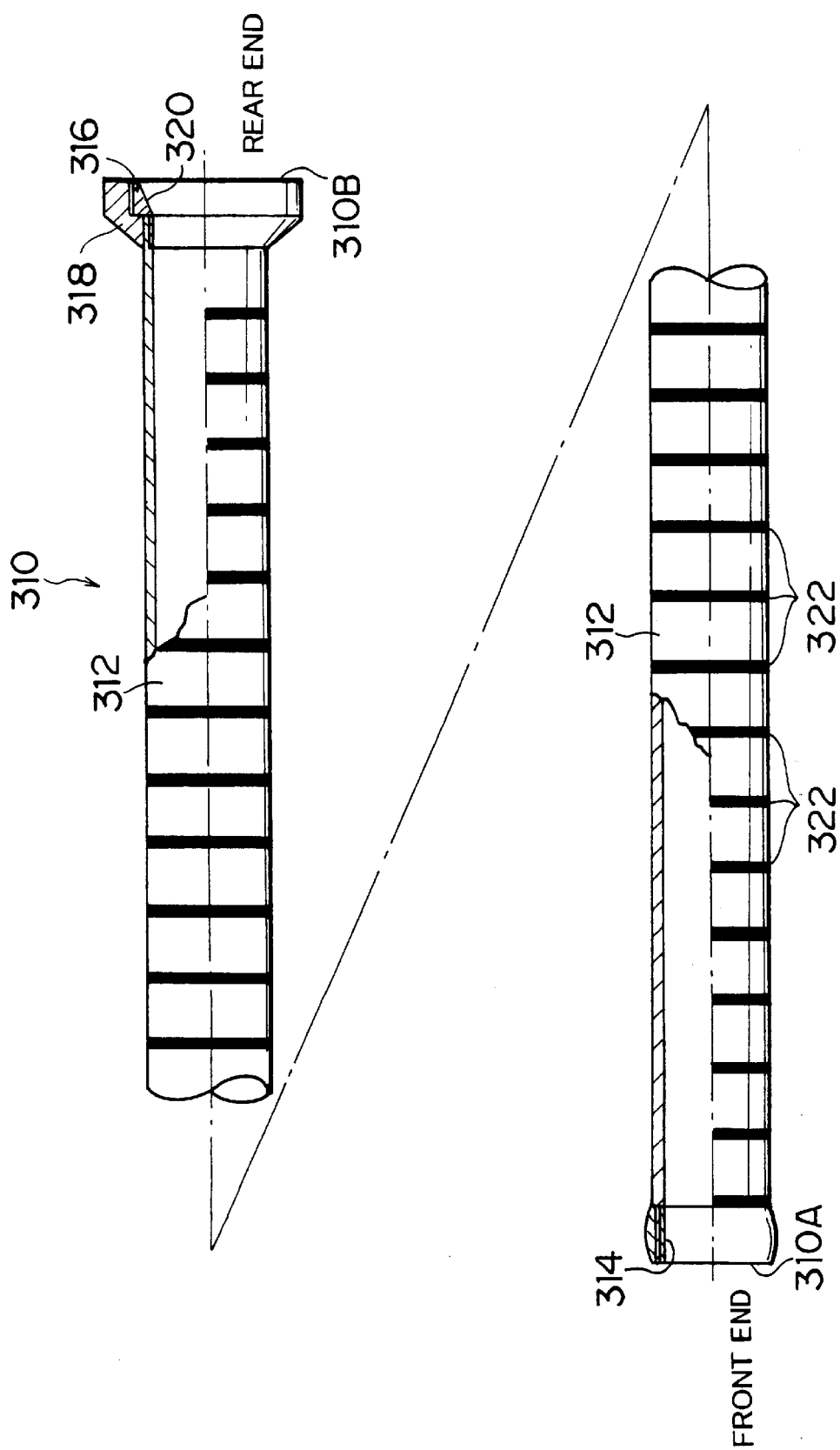
FIG. 17 is a side view showing a guide tube according to an embodiment of the present invention.

FIG. 17 is a side view showing a guide tube (equivalent to an insertion assisting device) 310 according to an embodiment of the present invention.

As shown in FIG. 17, the guide tube 310 is formed by a flexible tube 312, and the inner diameter of the guide tube 310 is slightly larger than the diameter of an endoscope insertion part. The tube 312 is composed of three layers, in which a tube made of resin such as urethane is coated with a chemical-resistant coating and the inside of the tube 312 is protected by a lubrication coating. The tube 312 restores when an external force is supplied to the outer peripheral surface of the tube 312. A disinfecting liquid, etc. and body fluids such as gastric juices never encroach on the tube 312 coated with the chemical-resistant coating. Moreover, the inside of the tube 312 is coated with the lubricant coating, so that the endoscope insertion part can smoothly be inserted into the tube 312.

A front end ring 314 is mounted in the tube 312 at a front end 310A of the guide tube 310. The end ring 314 is formed by mounting a resin ring on a metal ring. The metal ring may be made of any material through which x-rays are transmissible. The metal ring has the same inner diameter as the tube 312. It is therefore possible to know the front end position of the guide tube 310 by looking at the metal ring through the fluoroscope with x-rays.

An inner cylinder 316 is engaged with an outer cylinder 318 across the tube 312 at a rear end 310B of the guide tube 310. The inner diameter 316 has the same inner diameter as the tube 312, and a tapered part 320 is formed at a corner part of the inner cylinder 316 in order to facilitate the insertion of the endoscope insertion part. On the other hand, the outer diameter of the outer cylinder 318 is larger than the diameter of an insertion hole 332A of a mouthpiece 330 described later to thereby prevent the guide tube 310 from coming off the mouthpiece 330.

Figure 18:
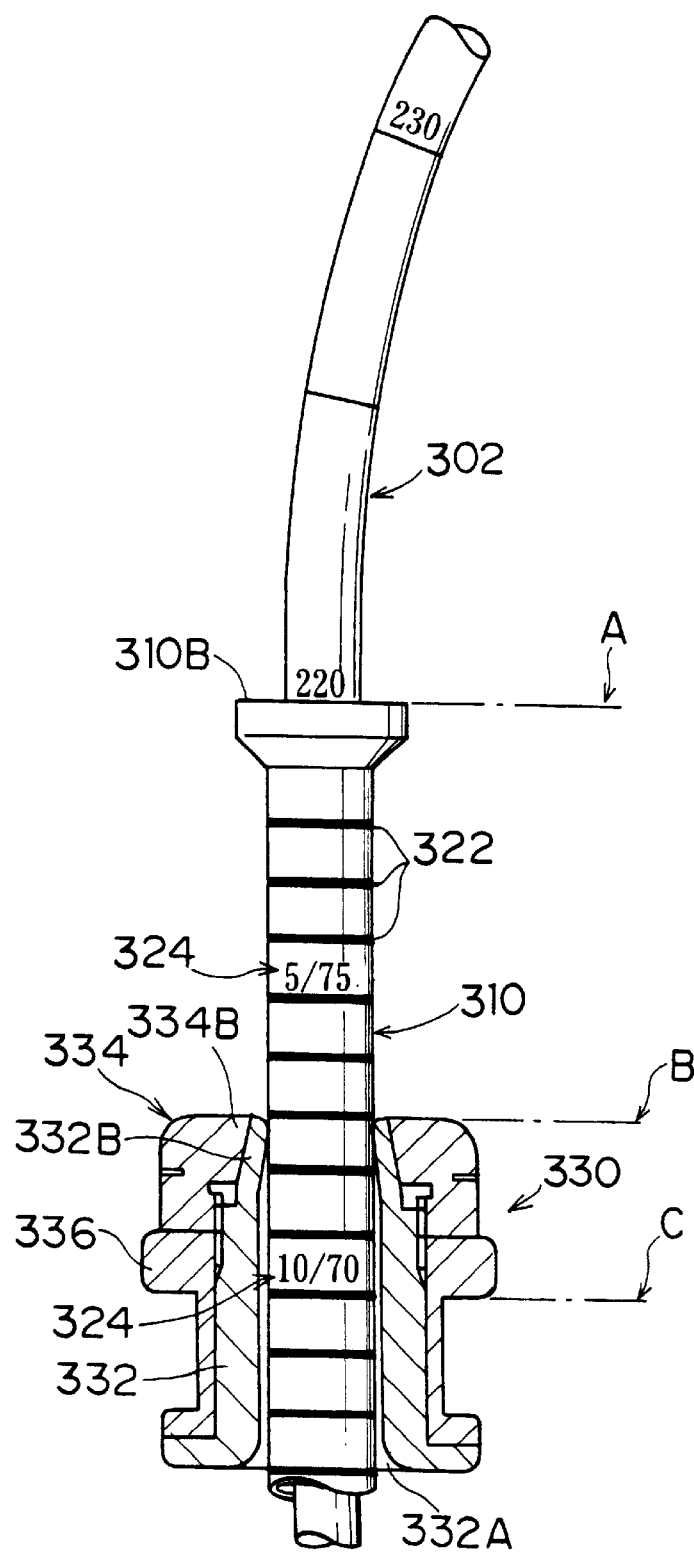
FIG. 18 is an enlarged view showing the guide tube in FIG. 17.

FIG. 18 is an enlarged view of a part of the guide tube 310, to which the mouthpiece 333 is attached.

As shown in FIG. 18, scale lines 322 are formed at regular intervals along the whole peripheral surface of the guide tube 310. Numbers 324 indicating lengths (hereinafter referred to as scale numbers) are written at intervals of some scale lines 322. In the scale number, a number at the right side of "/" indicates a length (hereinafter referred to as an insertion length of the guide tube 310) from the front end 310A (see FIG. 17) of the guide tube 310 to the scale line 322, and a number at the left side of the "/" indicates a length (hereinafter referred to as a residual length of the guide tube 310) from the rear end 310B to the scale line 322. In the case of a guide tube 310 that is 80 cm in length, the scale lines 322 are formed at intervals of 1 cm, and 5/75, 10/70, . . . are written in order at intervals of 5 cm from the rear end. It is therefore possible to confirm the insertion length and the residual length of the guide tube 310 at a glance. Indexes such as the scale lines 322 and the scale numbers 324 are formed in such a manner as to be recognized clearly by the operator. For example, they are printed with dots on the peripheral surface of the guide tube 310.

A description will now be given of the mouthpiece 330 that fixes the guide tube 310. As shown in FIG. 18, the mouthpiece 330 comprises a supporting member 332, a fixing member 334 and a tooth contact member 336. The tooth contact member 336, which is held in the mouth of the subject 1, is mounted on the supporting member 332. The supporting member 332 has an insertion hole 332A, into which the guide tube 310 can be inserted, and the cylindrical fixing member 334 is engaged with the supporting member 332. A conical inclined plane 332B is formed at the end of the supporting member 332. An inclined plane 334B of the fixing member 334 presses the inclined plane 332B inward when the fixing member 334 is engaged with the supporting member 332. When the fixing member 334 is engaged with the supporting member 332, the inclined plane 332B of the supporting member 332 is deformed inward to press the outer peripheral surface of the guide tube 310 and fix the guide tube 310 to the supporting member 332.

Reference numeral 302 in FIG. 18 denotes the endoscope insertion part, and an index is formed on the outer peripheral surface thereof. The index indicates distances from the end of the endoscope insertion part 302. The index is composed of scale lines at intervals of 5 cm from the end and scale numbers formed at intervals of 10 cm.

A description will now be given of the operation of the guide tube 310 that is constructed in the above-mentioned manner.

First, the fixing member 334 of the mouthpiece 330 is engaged with the supporting member 332, and the fixing member 334 is tightened to the supporting member 332 so that the inner diameter of the supporting part 332 can be larger than the outer diameter of the guide tube 310.

Figure 19:
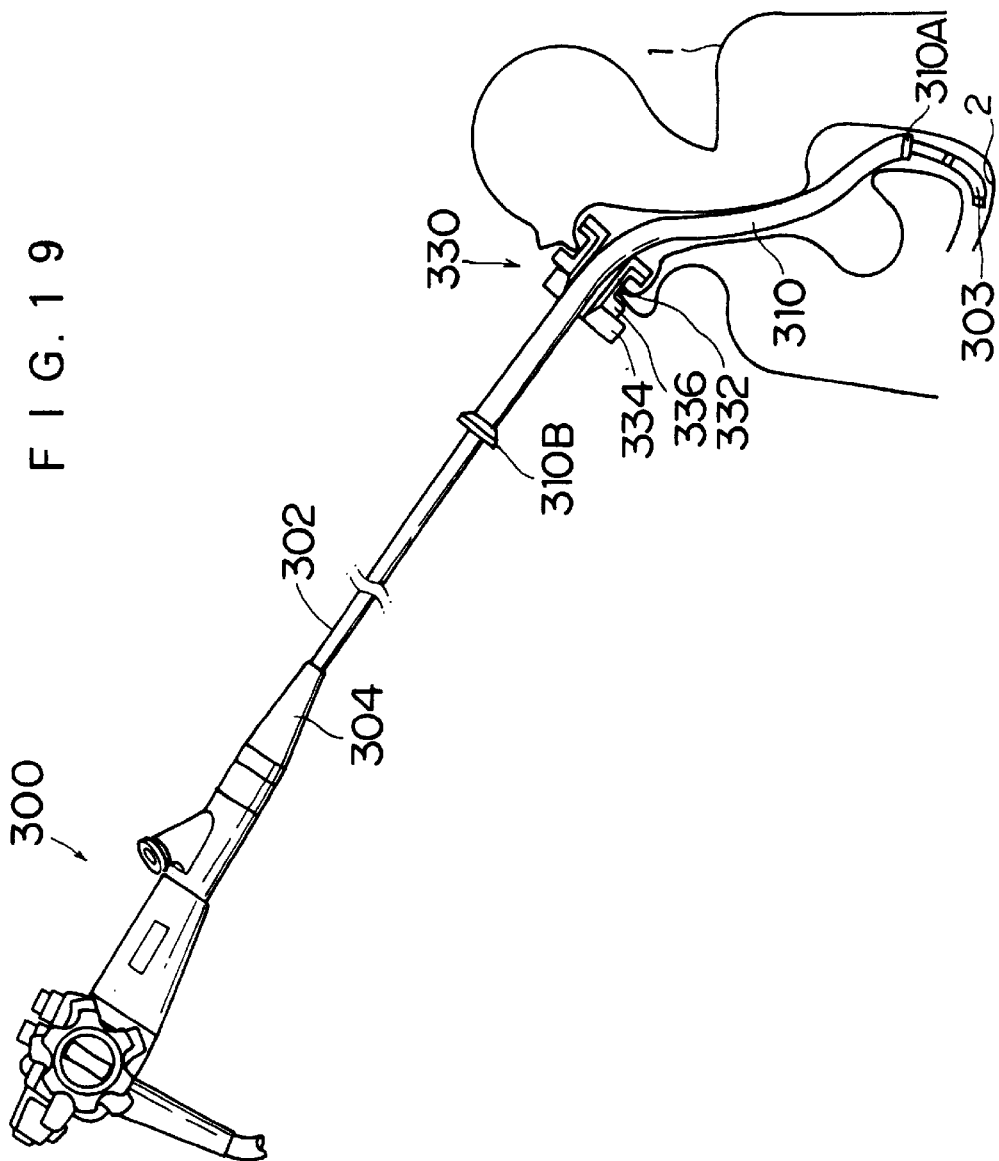
FIG. 19 is an explanation drawing showing a method of handling the guide tube in FIG. 17.

The endoscope insertion part 302 is inserted into the guide tube 310 before a small intestine endoscope 300 in FIG. 19 is inserted into the subject 1. Then, the guide tube 310 is drawn along the endoscope insertion part 302 toward a hand operation part 304.

Next, the mouthpiece 330 is held in the mouth of the subject 1. The endoscope insertion part 302 is inserted into the body cavity of the subject 1 through the mouthpiece 330. The endoscope insertion part 302 is inserted until an end 303 of the endoscope insertion part 302 reaches the descending part of duodenum 2.

Then, the guide tube 310 is inserted along the endoscope insertion part 302 into the body cavity. The guide tube 310 is inserted while the position of the end 310A is confirmed by looking at it through the fluoroscope with x-rays. The insertion of the guide tube 310 is stopped when the end 310A is positioned in the descending part of duodenum 2. The guide tube 310 may be inserted while the insertion length thereof is confirmed with reference to the index formed on the outer peripheral surface of the guide tube 310.

Then, the fixing member 334 of the mouthpiece 330 is further tightened to the supporting member 332 to thereby fix the guide tube 310 to the mouthpiece 330. The further insertion of the endoscope insertion part 302 enables the examination of the depths of the small intestine with the endoscope 300. In this case, the operator can correctly recognize the insertion length of the endoscope insertion part 302 at a glance with reference to the indexes formed on the guide tube 310 and the endoscope insertion part 302. If the guide tube 310 and the mouthpiece 330 are relatively positioned as shown in FIG. 18, the operator can correctly recognize the insertion length of the guide tube 310 inserted into the mouthpiece 330 as being 73 cm and the residual length of the guide tube 310 as being 7 cm with reference to the scale lines 322 and the scale numbers 324 at a glance. Thus, the length from a point B to the end 303 of the endoscope insertion part 302, in other words, the insertion length of the endoscope insertion part 302 is 213 cm, which is found by subtracting the residual length 7 cm from the scale 220 cm of the endoscope insertion part 302 at a point A.

Since the index indicating the insertion length of the endoscope insertion part 302 is formed on the outer peripheral surface of the guide tube 310 according to the present embodiment, it is possible to correctly recognize the insertion length of the endoscope insertion part 302 inserted into the subject 1. It is therefore possible to specify the position of a pathological area observed through the endoscope 300.

The index indicating the insertion length of the guide tube 310 is also formed on the guide tube 310, and thus, the end position of the guide tube 310 can be recognized at the same time.

The intervals between the scale lines 322 and between the scale numbers 324 are not restricted to the present embodiment. The scale lines 322 and the scale numbers 324 may be formed at any intervals on condition that the insertion length and the residual length of the guide tube 310 are recognized at a glance. For example, the intervals between the scale lines 322 and between the scale mark numbers 324 may be equal to the intervals between those of the index formed on the endoscope insertion part 302. The scale numbers 324 indicate both the insertion length and the residual length of the guide tube 310, but it may indicate only one of them.

The index formed on the guide tube 310 is not restricted to the above-described embodiment. It is possible to use any index which enables the user to correctly recognize the insertion length of the endoscope insertion part 302. For example, marks (concave or convex parts) or chips may be formed on the outer peripheral surface of the guide tube 310 at regular intervals. The outer diameter of the guide tube 310 may be changed at regular intervals.

In the present embodiment, the insertion length of the endoscope insertion part 302 is found with the point B being the reference point, but more correctly, the insertion length of the endoscope insertion part 302 may also be found with a point C being the reference point. In this case, an index is formed on the outer peripheral surface of the mouthpiece 330, or the scale numbers that are formed on the outer peripheral surface of the guide tube 310 while taking the distance between the point B and the point C into account.

In the present embodiment, the index is formed along the whole length of the guide tube 310, but the index may be formed only in a vicinity of the part supported by the mouthpiece 330.

In the present embodiment, the index is formed on the guide tube 310, but it may be formed on any insertion assisting device for an endoscope. For example, the index may be formed on a trocar for use in the percutaneous insertion of an endoscope such as a laparoscope and a thoracoscope into the body cavity.

In the insertion assisting device for the endoscope according to the present invention, the index is formed to indicate the insertion length of the endoscope insertion part so that the operator can correctly recognize the insertion length of the endoscope. Moreover, the operator can also recognize the insertion length of the insertion assisting device.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A mouthpiece for an endoscope, comprising a mouthpiece body that has an insertion hole into which a guide tube for guiding an endoscope insertion part is inserted, and a fixing member for fixing said guide tube inserted into said insertion hole of said mouthpiece body to said mouthpiece body, said mouthpiece wherein:

a large hole and a small hole are formed in said fixing member, said large hole and said small hole being connected to one another;

said fixing member slides between such a first position that said insertion hole of said mouthpiece body overlaps said large hole of said fixing member and such a second position that said insertion hole of said mouthpiece body overlaps said small hole of said fixing member, said fixing member being attached to said mouthpiece body in such a manner as to rotate at said second position; and said guide tube is inserted into said insertion hole of said mouthpiece body and said large hole of said fixing member at said first position, and then said fixing member is slid from said first position to said second position and is rotated by a predetermined amount at said second position to thereby hold said guide tube between an inner periphery of said insertion hole and an inner periphery of said small hole to fix said guide tube to said mouthpiece body.

2. The mouthpiece for the endoscope as defined in claim 1, wherein said fixing member is connected to said mouthpiece body through a slip prevention member that has a fixing member slide groove or a rotation groove so that said fixing member is prevented from being slipped from said mouthpiece body.

3. The mouthpiece for the endoscope as defined in claim 1, wherein an index part indicating a procedure for operating said mouthpiece body or said fixing member is formed in said mouthpiece body and said fixing member.

4. The mouthpiece for the endoscope as defined in claim 1, wherein an index part indicating a sliding amount and a rotation amount of said fixing member is formed in said mouthpiece body and said fixing member.

* * * * *